United States Patent [19]

O'Leary

[11] 3,993,061

[45] Nov. 23, 1976

[54] SYRINGE PUMP DRIVE SYSTEM AND DISPOSABLE SYRINGE CARTRIDGE

[75] Inventor: Stephen H. O'Leary, San Diego, Calif.

[73] Assignee: Ivac Corporation, San Diego, Calif.

[22] Filed: Feb. 28, 1975

[21] Appl. No.: 554,230

[52] U.S. Cl. .................. 128/214 F; 128/218 P; 128/218 R; 128/234; 128/273; 128/278; 128/DIG. 12; 417/437
[51] Int. Cl.² .................................. A61M 5/20
[58] Field of Search .......... 128/214, 215, 218, 219, 128/234–238, 273, 278, DIG. 1, DIG. 12; 417/437; 92/98 D, 105, 170

[56] References Cited

UNITED STATES PATENTS

| 1,572,075 | 2/1926 | Painter | 417/437 |
|---|---|---|---|
| 1,585,628 | 5/1926 | Pfarre | 417/437 |
| 2,672,866 | 3/1954 | Kater | 128/215 |
| 3,050,059 | 8/1962 | Wall et al. | 128/218 P |
| 3,335,724 | 8/1967 | Gienapp | 128/218 A |
| 3,543,752 | 12/1970 | Hesse et al. | 128/214 E |
| 3,731,679 | 5/1973 | Wilhelmson et al. | 128/214 F |
| 3,752,145 | 8/1973 | Runnells et al. | 128/218 C |
| 3,939,078 | 2/1976 | Servas | 210/436 |

FOREIGN PATENTS OR APPLICATIONS

| 805,611 | 8/1936 | France | 92/105 |
|---|---|---|---|
| 941,370 | 11/1963 | United Kingdom | 128/218 R |
| 1,041,311 | 9/1966 | United Kingdom | 128/218 R |

Primary Examiner—Dalton L. Truluck
Attorney, Agent, or Firm—Fulwider, Patton, Rieber, Lee & Utecht

[57] ABSTRACT

A parenteral administration system, utilizing a syringe pump operated by a motor to repetitively fill and empty a disposable syringe cartridge over a plurality of operational cycles of successive fill and pump stroke periods. The syringe cartridge has no valves, and the apparatus repetitively and sequentially opens and closes, by means of an external pair of tube pinchers, a pair of intake and output I.V. tubes communicating with the inlet and outlet nipples. The disposable syringe cartridge includes a molded plastic cylinder having inlet and outlet nipples, a plastic piston and piston rod, and a rubber sealing cap defining a conical piston face, a pair of piston sealing rings and a sealing boot. The pair of sealing rings enhance axial alignment and stability, while the sealing boot prevents air or bacterial intake through the bottom of the cylinder during repetitive strokes. The plastic cross-sections are selected to provide maximum strength for minimum material employed. The interior cylinder chamber is sloped to drive out gas through the outlet nipple. An integral tab on the cylinder provides an operator handle for mounting and removing the syringe. One end of the piston rod is cut away and provided with mounting bosses, adapted to engage and be retained by a cooperating drive system mounting shoe so that the syringe can be inserted in the shoe horizontally, be rotated to a vertical position, and engage fixed guide and retaining slots by means of a pair of integral bosses projecting from the syringe cylinder.

20 Claims, 13 Drawing Figures

U.S. Patent  Nov. 23, 1976  Sheet 1 of 2  3,993,061
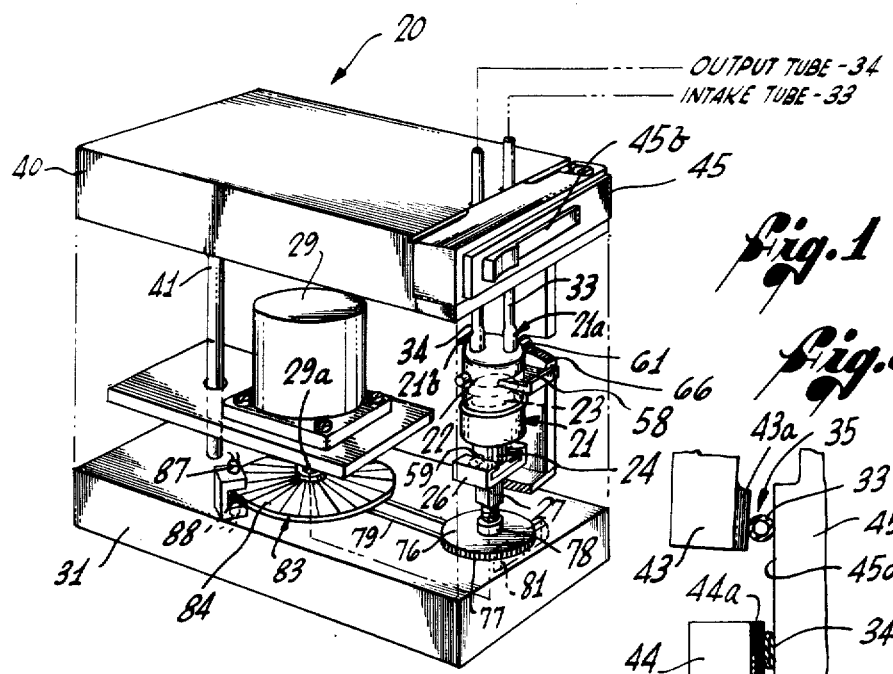

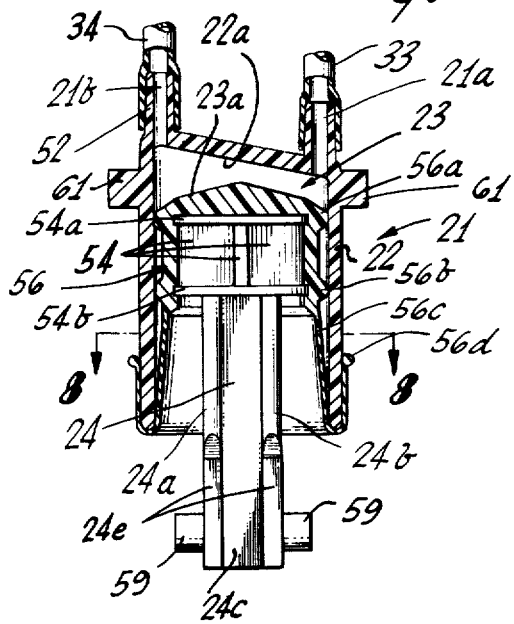
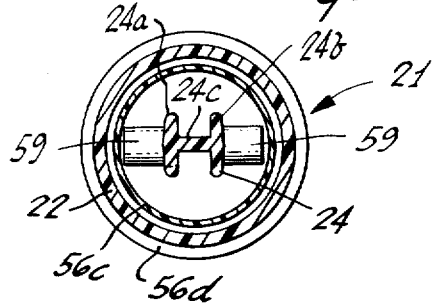
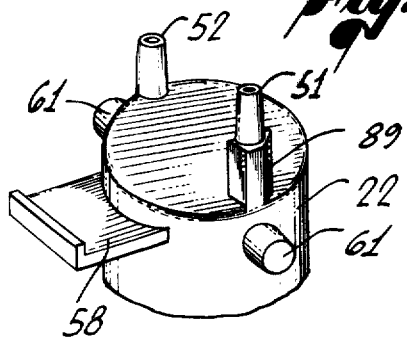
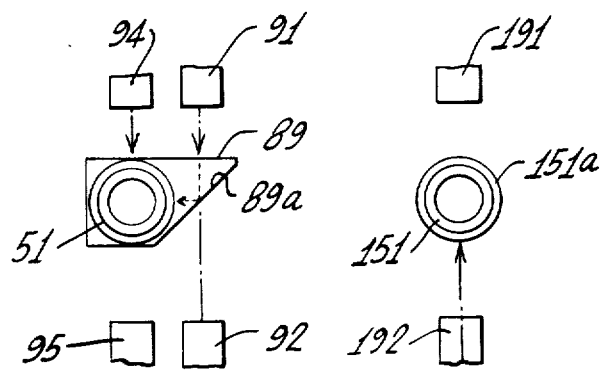
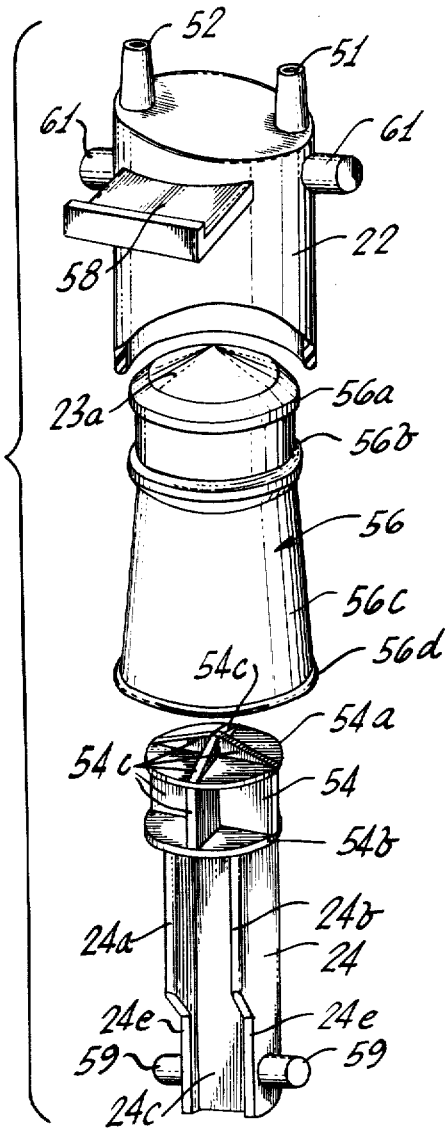

SYRINGE PUMP DRIVE SYSTEM AND DISPOSABLE SYRINGE CARTRIDGE

BACKGROUND OF THE INVENTION

This invention relates generally to improvements in syringe pumps and, more particularly, to a new and improved drive system and syringe for such pumps, wherein a disposible syringe cartridge having no valves is reliably and precisely mounted, monitored, and driven through repetitive fill and pump strokes.

The usual medical procedure for the gradual parenteral administration of liquids into the human body, such as liquid nutrients, blood or plasma, makes use of apparatus which is commonly referred to in the medical arts as an intravenous administration set. The intravenous set usually comprises a bottle of liquid, normally supported in an inverted position, an intravenous feeding tube, typically of clear plastic, and a suitable valve mechanism, such as a roll clamp, which allows the liquid to drip out of the bottle at a selectively adjustable rate into a transparent drip chamber below the bottle. The drip chamber serves the dual function of allowing a nurse or other attendant to observe the rate at which the liquid drips out of the bottle, and also creates a reservoir for the liquid at the lower end of the drip chamber to insure that no air enters the main feeding tube leading to the patient.

While observation of the rate of drop flow via the drip chamber is a simple way of controlling the amount of liquid fed to a patient over a period of time, its ultimate effectiveness requires that a relatively constant vigil be maintained on the drop flow, lest it cease entirely due to exhaustion of the liquid supplied or become a continuous stream and perhaps increase the rate of liquid introduction to the patient to dangerous levels.

By way of example, it has been the general practice in hospitals to have nurses periodically monitor drop flow rate at each intravenous feeding or parenteral infusion station. Such monitoring of drop flow is a tedious, and time consuming process, prone to error and associated, possibly serious consequences, and resulting in a substantial reduction of the available time of qualified medical personnel for other important duties. Typically, the nurse monitoring drop flow rate will use a watch to time the number of drops flowing in an interval of one or more minutes, and she will then mentally perform the mathematics necessary to convert the observed data to an appropriate fluid flow rate, e.g., in drops per minute. If the calculated flow rate is substantially different than the prescribed rate, the nurse must manually adjust the roll clamp for a new rate, count drops again, and recalculate to measure the new flow rate.

Obviously, each of the aforesaid measurements, calculations and flow rate adjustments usually take several minutes time which, when multiplied by the number of stations being monitored and the number of times each station should be monitored per day, can result in a substantial percentage of total personnel time available. In addition, under the pressure of a heavy schedule, the observations and calculations performed by a harried nurse in measuring and adjusting flow rate may not always prove to be reliable and, hence, errors do occur resulting in undesired, possibly dangerous infusion flow rates.

In addition to the aforedescribed difficulties, the parenteral administration of medical liquids by gravity induced hydrostatic pressure infusion of the liquid from a bottle or other container suspended above the patient, is very susceptible to fluid flow rate variation due to changes in the liquid level in the bottle, changes in temperature, changes in the venous or arterial pressure of the patient, patient movement, and drift in the effective setting of the roll clamp or other valve mechanism pinching the feeding tube. Moreover, there are a number of situations, such as in intensive care, cardiac and periatric patients, or where rather potent drugs are being administered, where the desired drop flow rate must be capable of very precise selection.

It will be apparent, therefore, that some of the most critical problems confronting hospital personnel faced with an overwhelming duty schedule and limited time availability are the problems of quickly, easily, reliably and accurately controlling fluid flow in the parenteral administration of medical liquids.

In recent years, a number of electrical monitoring systems, drop flow controllers and infusion pumps have been developed to accomplish the various tasks of sensing and regulating drop flow rates. However, while such devices have generally served their purpose, they have not always proven entirely satisfactory from the standpoint of cost, complexity, stability, reliability or accuracy. In addition, such systems have sometimes been subject to drift and substantial flow rate variations due to changes in temperature, feeding tube crimps, variations in venous or arterial pressure of the patient, or variations in the height of the bottle or solution level within the bottle.

Even positive pressure pumps of the closed-loop peristaltic type only serve to maintain accuracy of flow in terms of stabilizing to a preselected drop flow rate, rather than delivering a precise preselected volume of fluid, e.g., in cubic centimeters per hour. The reason for this is that the accuracy of such a system is limited inherently to the accuracy of the size of the drops produced by an intravenous administration set, and the actual drops produced by the latter apparatus can vary rather substantially from its designated drop size, e.g., due to drip chamber structural variations, by as much as thirty percent.

More recently, positive pressure infusion pumps of the syringe type have also been provided, wherein a syringe having a very precise displacement volume is repeatedly filled and emptied on alternate syringe piston strokes during a combined "fill" and "pump" operational cycle, so that control of the rate at which the syringe is filled and emptied provides an accurate means for precise fluid volume delivery over a prescribed period of time. Such syringe pumps are essentially independent of drop flow inaccuracies introduced by I.V. administration sets and appear to provide the best overall solution to accurate and stable fluid volume delivery over long periods of time, at both high and low flow rates.

At the heart of the syringe pump is the syringe itself. Such syringes must be sufficiently rugged and reliable to enable repetitive fill and pump strokes over sustained periods of pump operation without leaking, or admitting air or pathogens to the interior of the syringe. Where disposable syringes are involved, the syringe should preferably be of relatively simple and economical construction, easily handled for insertion into and removal from the remainder of the pumping apparatus and should be mounted in such a fashion as to facilitate removal of air prior to startup. Unfortunately, however, such syringes of the prior art have been relatively complex and expensive, have been prone to leakage and have been relatively difficult to mount and remove.

In addition, syringe pumps of the prior art primarily depend on valving embodied directly within the syringe itself, for switching from the fill mode to the pumping mode. This not only increases the cost and complexity of the syringe, particularly where disposable syringes are employed, but usually also results in reduced reliability of operation.

Furthermore, it has been difficult at low flow rates, when the syringe piston is moving so slowly that its motion is not visually discernible by the operator, to determine whether or not the syringe is being driven at all.

Hence, those concerned with the development and use of parenteral fluid administration systems, and particularly those concerned with the design of syringe pumps, have long recognized the need for improved, relatively simple, economical, reliable, stable and accurate syringes, monitoring and drive systems for such syringe pumps. The present invention clearly fulfills this need.

SUMMARY OF THE INVENTION

Briefly, and in general terms, the present invention provides a new and improved means for accurately controlling fluid flow in the parenteral administration of medical liquids, wherein a disposable, valveless syringe cartridge is easily, reliably and precisely mounted, its state of proper insertion into the pumping apparatus being monitored, after which the syringe is driven through repetitive fill and pump strokes. Appropriate valving is provided within the pumping apparatus external to the syringe cartridge, without the need for providing relatively complex, expensive and sometimes unreliable valve structures in the syringe itself.

The syringe cartridge of the present invention is of strong, lightweight, durable construction and is constructed to minimize the possibility of fluid leakage, enhance the ease and simplicity of mounting and removal from the pumping apparatus, facilitate the removal of air prior to start-up of the pumping apparatus, and to prevent intake of air or pathogens into the interior of the syringe during repetitive pumping cycles. A running indicator is provided to indicate visually to the operator that the pump is cycling, motion of the indicator being observable even at low flow rates where syringe operation may not normally be readily discernible by the operator. In addition, a rotation sensor is provided to monitor the mechanical output of the motor driving the syringe and detect any stalled motor condition.

More particularly, the present invention provides a new and improved syringe pump operated by a motor to repetitively fill and empty a disposable syringe cartridge over a plurality of operational cycles of successive fill and pump stroke periods. The disposable syringe cartridge itself embodies no valving structure, but includes a pair of intake and output I.V. tubes communicating with the inlet and outlet nipples, respectively, of the syringe. The remainder of the pumping apparatus drives the syringe and repetitively and sequentially opens and closes the intake and output I.V. tubes by means of a pair of tube pinchers external to the syringe cartridge, the I.V. tubes alternating their opened and closed states, one tube pincher controlling each I.V. tube.

The disposable syringe cartridge includes a molded plastic cylinder having inlet and outlet nipples and defining an interior chamber adapted to slidingly receive a plastic piston and piston rod. A rubber sealing cap overlies and encases the plastic piston, and defines a conical piston face. The sealing cap includes a pair of resilient annular ribs defining piston sealing rings, and further includes a limp diaphragm conical sealing boot. The dual, spaced apart sealing rings define two point contact along the longitudinal axis of the syringe to enhance axial alignment and stability of the piston and piston rod as the piston slides within the cylinder of the syringe, whereas the sealing boot at the base of the cylinder prevents the intake of air or pathogens through the bottom of the cylinder during repetitive strokes. All plastic cross-sections of syringe cartridge components are selected to provide maximum strength for a minimum amount of plastic material.

The inlet and outlet nipples of the syringe cartridge extend parallel to the longitudinal axis of the syringe, on opposite sides of the syringe. The interior surface of the cylinder defines, with the piston, a fluid chamber, and the cylinder surface above the piston is sloped upwardly towards the base of the outlet nipple, so that, when the longitudinal axis of the syringe is vertical, gas bubbles will tend to rise to the highest point of the cylinder and out through the outlet nipple for easy removal.

The syringe cartridge and associated mounting means are designed to facilitate simple and easy insertion of the cartridge into the pump housing, requiring the use of only one hand by the operator. In this regard, an integral tab extends from the syringe cylinder and provides an operator handle for mounting and removing the syringe from the overall pumping apparatus. In addition, the end of the piston rod remote from the piston head is partially cut-away and provided with integral, outwardly extending mounting bosses. These mounting bosses are adapted to engage and be retained by a mounting shoe secured to the leading end of a linear drive shaft adapted to be coupled to the piston rod for driving the syringe through successive fill and pump strokes. The mounting shoe includes a pair of guide slots adapted to engage the piston rod mounting bosses so that the syringe cartridge can be inserted into the mounting shoe horizontally, be rotated so that its longitudinal axis is vertical, and thereby bring the lower, cut-away end of the syringe piston rod into a retention slot within the mounting shoe to prevent the syringe cartridge from being dislodged, either horizontally by virtue of the retention slot, or vertically by means of the lower end of the piston rod and the mounting bosses.

A second pair of outwardly extending mounting bosses, parallel to the first set of mounting bosses on the piston rod, are integral with the syringe cylinder and are adapted to engage a pair of fixed guide and retaining slots provided in opposite walls of a syringe receiving compartment defined in the pump housing. The intake and output I.V. tubes from the syringe cartridge pass vertically over a pair of tube pincher blades and are clamped in position by a suitable tubing compartment access door which is appropriately latched. Thus, the syringe cartridge is firmly maintained in position during the operational cycles of the pump. The tubing access door must be unlatched and opened to enable the syringe cartridge to be rotated from the vertical position to a horizontal position for removal from the mounting shoe.

By controlling the initial location of the mounting shoe, relative to the guide and retaining slots in the sidewalls of the syringe compartment, the pumping apparatus can be conditioned to receive the syringe cartridge only if its piston is in a predetermined position within the syringe cylinder, i.e., in the top dead center position adapted to initially perform an intake stroke to fill the syringe with fluid. The latter is the proper state of the syringe for initial start-up of the pumping apparatus.

A reference light source and photoelectric sensor is provided within the syringe compartment to sense the physical presence of the syringe cartridge, and an appropriate electrical signal is generated whenever the reference light beam is interrupted by one of the syringe nipples, to thereby indicate proper installation of the syringe cartridge for control over pump operation. Another reference light source and photoelectric sensor is provided adjacent one of the syringe nipples as a bubble detector to insure that all of the air has been removed from the syringe and to prevent air delivery to the patient.

A motor rotation sensor is provided, the rotation sensor typically being in the form of a disc mounted on the motor output shaft for rotation there with, the disc having alternate transparent and opaque sectors. A photocell detects light from a reference light source passing through the disc, as it rotates, and generates an output electrical signal capable of indicating any stalled motor condition.

A visual running indicator is also provided, typically in the form of a rotating disc having index lines uniformly spaced along its peripheral edge, so that pump operation is visually discernible by the operator, even at low flow rates where motion of the syringe piston is so slow as to not be readily discernible by the eye of the operator.

The new and improved syringe pump drive system and disposable syringe cartridge satisfies a long existing need in the medical arts for improved, relatively simple, economical, reliable, stable and accurate syringe pumping systems.

The above and other objects and advantages of the present invention will become apparent from the following more detailed description, when taken in conjunction with the accompanying drawings of illustrative embodiments.

DESCRIPTION OF THE DRAWINGS

FIG. 1 is a perspective view showing main components of the interior structure of a syringe pump embodying the present invention, portions of the outer pump housing being shown in phantom;

FIG. 2 is a fragmentary, plan view of a rotation sensor in accordance with the invention;

FIG. 3 is a fragmentary, elevational view, portions being shown in section, through the syringe pump in the vicinity of the syringe cartridge compartment, the syringe cartridge being shown in solid lines in its properly installed position, the cartridge also being shown in phantom in an intermediate position during the installation procedure;

FIG. 3A is a fragmentary sectional view, taken substantially along the line 3A—3A in FIG. 3, and illustrates the pincher valves external to the syringe cartridge;

FIG. 4 is a fragmentary sectional view, taken along the line 4—4 in FIG. 3 and illustrates portions of the drive system for the syringe;

FIG. 5 is a perspective view of the mounting shoe for coupling the drive system to the syringe cartridge;

FIG. 6 is a plan view of the mounting shoe shown in FIG. 5;

FIG. 7 is an elevational view of an assembled syringe cartridge in accordance with the present invention, portions being shown in section;

FIG. 8 is a sectional view, taken along the lin 8—8 in FIG. 7;

FIG. 9 is an exploded perspective view of the main structural components of a syringe cartridge constructed in accordance with the present invention, a portion of the syringe cylinder being shown in section;

FIG. 10 is a fragmentary perspective view of the upper portion of a syringe cartridge incorporating provisions for monitoring the physical position of the cartridge and the presence of gas bubbles;

FIG. 11 is a plan view of a syringe nipple embodying the cartridge position monitoring and bubble detection structure of FIG. 10 and further illustrating the location of the reference light sources and photocell sensors relative to the nipple; and FIG. 12 illustrates an alternate arrangement for monitoring the physical position of a syringe cartridge.

DESCRIPTION OF THE PREFERRED EMBODIMENT

Referring now to the drawings, there is shown a syringe pump system for fluid flow control, embodying the features of the present invention. In the ensuing description, while reference is made to the term "I.V.," normally connoting intravenous administration, it is to be understood that this is by way of example only, and the system of the present invention is suitable for other forms of parenteral administration as well as intravenous administration.

The system shown in FIG. 1 depicts a syringe pump 20 embodying a disposable syringe cartridge 21. The syringe cartridge 21 essentially includes a molded plastic cylinder 22 in which a piston 23 is slidably received and adapted to be reciprocated back and forth along the axis of the cylinder by an integral piston rod 24 which is removably mounted at one end in a coupling shoe 26 carried by a linear drive shaft 27 which is advanced and retracted by a suitable drive system. The drive system includes a reversible motor 29 (typically a d.c. stepping motor) and appropriate gearing 31, to advance and retract the shaft 27 which is, in turn, coupled to the piston rod 24 of the syringe cartridge 21. The motor 29 is energized by a pulse train of motor drive pulses generated by an appropriate electrical control system (not shown).

The displacement volume of the syringe cartridge 21 is determined by the volume swept by the piston 23 on each stroke and is identical for the fill stroke and for the pump stroke. Therefore, an identical number of discrete steps or motor drive pulses from the electrical control system to the motor 29 is required for each fill stroke during which the syringe is filled with liquid, and for each pump stroke during which the syringe delivers its precise volume of liquid under positive pressure to a patient.

The syringe cartridge 21 includes an inlet port 21a and an outlet port 21b. The inlet port 21a communicates through a suitable intake I.V. tube 33 with any appropriate liquid source (not shown), usually an I.V. bottle containing appropriate drugs and/or nutrients in liquid form. Typically, the intake I.V. tube 33 is part of an I.V. administration set which includes a transparent drip chamber in the line between the syringe cartridge 21 and the liquid source.

A similar, output I.V. tube 34 is connected at one end to the outlet port 21b of the syringe cartridge 21 and conveys fluid from the syringe to a patient.

As best observed in FIGS. 3 and 3A, a pair of syringe pump valves 36, 37, external to the syringe cartridge 21, are of the tube pincher type, and are selectively opened and closed at appropriate times in the overall pumping cycle, under the control of a suitable valve control system 40. The valve 36 controls the inlet port 21a and is open during the fill stroke to enable fluid to be drawn from the liquid source, through the intake line 33, into the syringe cartridge 21, the valve 36 being closed during the pump stroke to prevent fluid from exiting the syringe through the inlet port. The valve 37 controls the outlet port 21b and is open during the pump stroke to enable fluid delivery from the syringe cartridge 21 to the patient through the output line 34, the valve 37 being closed during the fill stroke.

The valve control system 40 is also driven, through the gearing 31, by the same motor 29 as is used to operate the syringe cartridge 21. In addition, the valve control system 40 includes means (not shown) for providing information to the electrical control system controlling the motor 29, and indicating that the syringe cartridge 21 is either in the fill stroke or the pump stroke. This latter information, in turn, enables the electrical control system to establish the proper direction of rotation of the motor 29. The electrical control system may be of conventional design for electrically energizing the motor 29 and controlling its direction of rotation, or the control system may be of the form described in copending application, Ser. No. 554,092, entitled Fluid Flow Control System, inventor Heinz W. Georgi, filed Feb. 28, 1975, and assigned to the same assignee as the present application. A copy of the specification and drawings for the latter application is attached hereto as Appendix A.

The motor 29 drives, through the gearing 31 and an output camshaft 41, a reversible cam (not shown) in the valve control system 40, which cyclically alternates the open and closed positions of the syringe pump valves 36, 37.

The syringe pump valves 36, 37 typically consist of a pair of pivotal tube pinchers 43, 44 which alternately pinch off and open the intake and output tubes 33, 34 respectively, of the syringe cartridge 21. One face of each of the tube pinchers 43, 44 is shaped to define a pincher blade 43a, 43b, respectively, adapted to cooperate with the confronting face of a shoulder 45a defined on the interior side of a syringe pump tubing access door 45 to the syringe compartment. Together, the pincher blades 43a, 44a and the access door shoulder 45a adefine a pair of tube clamps between which the intake and output I.V. tubes 33, 34 pass. The access door 45 is held shut, after the syringe cartridge 21 has been installed, by any suitable latch 45b (FIG. 1).

The tube pinchers 43, 44 are spring biased to the tube shut-off position and are positively driven open by the valve control system 40, thus allowing full tube closure regardless of normal variations in I.V. tubing diameter and wall thickness.

The valves 36, 37 and valve control system 40 may be of conventional design or may be of the form described in copending application, Ser. No. 554,091, entitled Syringe Pump Valving And Motor Direction Control System, inventor Wallace L. Knute, filed Feb. 28, 1975, and assigned to the same assignee as the present application. A copy of the specification and drawings for the latter application is attached hereto as Appendix B.

Referring now more particularly to FIGS. 7-9 of the drawings, the new and improved syringe cartridge 21 of the present invention is of strong, lightweight, durable construction and is constructed to minimize the possibility of fluid leakage from the interior of the syringe, enhance the ease and simplicity of mounting and removal from the syringe compartment of the pump, facilitate the removal of air prior to actual operation of the pumping apparatus, and to prevent intake of air or pathogens into the interior of the syringe during repetitive pumping cycles.

The disposable syringe cartridge 21 includes the molded plastic cylinder 22 having inlet and outlet nipples 51, 52, respectively, at the upper end of the cylinder (with the longitudinal axis of the syringe in the vertical position as is the case following proper installation shown in FIG. 1). The cylinder 22 is hollow and thereby defines an interior chamber adapted to slidingly receive a plastic piston head 54 which is integral with the piston rod 24. The cylinder 22, and combined piston rod 24 and piston head 54 are typically injection molded of any suitable thermoplastic material, such as polypropylene.

A rubber sealing cap 56 overlies and encases the piston head 54 to define the piston 23, the sealing cap providing a conical piston face 23a directed towards the inlet and outlet nipples 51, 52, respectively, of the syringe.

The inlet and outlet nipples 51, 52 of the syringe cartridge 21, extend parallel to the longitudinal axis of the syringe on opposite sides of the syringe, diametrically opposed from each other. The interior surface of the syringe cylinder 22 defines, with the piston 23, a fluid containing chamber, and the uppermost cylinder surface 22a above the piston is sloped upwardly, typically at an angle of approximately 10°, towards the base of the outlet nipple 52. Hence, when the longitudinal axis of the syringe is vertical, following installation into the pumping apparatus, gas bubbles will tend to rise to the highest point of the syringe cylinder 22 and pass out through the outlet nipple 52, for easy removal at some convenient access point in the output I.V. tube 34. In addition, the piston face 23a slopes symmetrically downward from its apex at an angle of approximately 10° to the horizontal, matching the slope of the interior surface 22a of the cylinder 22, to minimize the residual volume of the syringe.

The sealing cap 56, which is typically fabricated of a natural rubber, also includes a pair of resilient, annular ribs 56a, 56b which fit over and are supported by corresponding annular flanges 54a, 54b in the piston head 54.

The sealing cap ribs 56a, 56b provide a pair of axially spaced apart piston sealing rings. These dual, spaced apart sealing rings define two point contact support along the longitudinal axis of the syringe cartridge 21 to provide improved sealing efficiency, and to enhance the axial alignment and stabililty of the piston and piston rod assembly within the cylinder 22 of the syringe as the piston 23 reciprocates back and forth within the cylinder during repetitive pump cycles. Hence, the two point support along the longitudinal axis of the system prevents rocking of the piston 23 which might otherwise cause the system to be prone to leakage and might also provide uneven wear on the sealing rings.

The sealing cap 56 further includes a thin walled conical sealing boot 56c integral at its frustrum with the rib 56b and terminating at its base in a thickened wall portion defining a bead 56d. The sealing boot 56c provides a limp membrane sealing element when the syringe cartridge 21 is assembled, to prevent the intake of air or pathogens through the bottom of the cylinder 22 as the piston assembly reciprocates through repetitive strokes within the cylinder.

The use of the sealing cap to encase the plastic piston head 54 and thereby define the outer surface of the piston 23, including the sealing rings 56a, 56b, enables the piston head 54 and piston rod 24 to be fabricated of less expensive materials than would be required if the piston head were in direct sliding engagement with the interior walls of the cylinder 22.

The material from which the sealing cap 56 is fabricated is chosen because of its material properties, e.g., wear resistance on the seals, compression set resistance so that it will retain its elastic properties, resistance to tearing on the boot because of the thin walled membrane, and resistance to the temperatures normally encountered in the sterilization process. In contrast, the plastic material from which the cylinder 22, piston head 54 and piston rod 24 are fabricated is chosen primarily for low cost of material, ease of manufacture, and resistance to sterilization temperatures.

All plastic cross-sections of the various components of the syringe cartridge 21 are selected to provide a maximum of strength for a minimum amount of plastic material. In this regard, while strength is required, a thin walled structure is also desirable in order for plastic molding to be most effective. Hence, a maximum degree of rigidity with a minimum amount of plastic, in a convenient cross-section, is selected for the syringe cartridge 21 of the present invention. In this regard, it will be apparent in FIG. 8 that the piston rod 24 is molded in an "H" cross-section, defined by a pair of longitudinally extending, parallel flanges 24a, 24b joined by an integral, coextensive cross-bar 24c.

As previously pointed out, the piston head flanges 54a, 54b retain the sealing cap 56 and provide adequate support for the piston 23. The parallel flanges 54a, 54b are, in turn, supported by four integral ribs 54c which intersect at the longitudinal axis of the piston head, the uppermost ends of these ribs being tapered to provide support for the conical face 23a of the sealing cap 56. This prevents the sealing cap 56, which is not very rigid, from collapsing. The rib structure defined by the four ribs 54c is selected, instead of a solid circular cylindrical cross-section, for molding purposes, to provide adequate strength with a minimal amount of plastic material required.

In assembling the cylinder 22, sealing cap 56, and combined piston head 54 and piston rod 24, (the components of FIG. 9) into the syringe cartridge 21 of FIG. 7, the sealing cap 56 is simply pressed over the piston head 54 until the flanges 54a, 54b engage internal slots in the sealing cap adjacent the ribs 56a, 56b, which results in the sealing cap and piston head snapping together. The resulting assembly of the sealing cap 56 and piston head 54 (defining the piston 23) and the piston rod 24, is pushed into the opening in the base of the cylinder 22. A suitable lubricant may be used to facilitate insertion of the assembly into the cylinder 22, as well as subsequent reciprocation within the cylinder. The base of the sealing boot 56c is then folded over the open base of the cylinder 22, so that the bead 56d, which behaves as an elastic O-ring, grips the outer surface of the cylinder and holds the sealing boot 56c in position so that it can't be pealed back easily or tear. In this regard, the hoop strength of the bead 56d must be sufficient to resist movement once it has been positioned to grip the outer surface of the cylinder 22.

The length of the skirt portion of the sealing boot 56c is such that it is not required to stretch at all during any portion of the pumping cycle as the piston 23 reciprocates back and forth within the cylinder 22. Hence, the boot 56c provides a limp membrane as a seal against admission of air or pathogens to the interior of the cylinder 22 during repetitive strokes of the syringe. In this regard, since the limp membrane seal provided by the sealing boot 56c is essentially unstressed, it is both rugged and reliable. In addition, should sufficient air be trapped in the air gap between the rib 56b and the sealing boot 56c, during assembly into the cylinder 22, the air volume might be compressed during fill strokes of the piston 23 when the piston is in its lowermost position. However, the combination of the additional volume provided by the unfolding limp membrane of the sealing boot 56c, together with the anchoring afforded by the bead 56d, resists popping of the sealing boot off the cylinder 22, even in the event of ballooning of the boot by any such trapped air.

After the cylinder 22, sealing cap 56 and combined piston 54 and piston rod 24 have been assembled in the aforedescribed manner, the intake I.V. tube 33 and output I.V. tube 34 are appropriately secured to the inlet and outlet nipples 51, 52, respectively, to complete the assembly of the syringe cartridge 21.

The syringe cartridge 21 is constructed to cooperate with associated mounting means within the syringe compartment of the pump housing to facilitate simple and easy insertion of the cartridge into the pump housing while requiring the use of only one hand by the operator. In this regard, an integral tab 58 projects from the outer surface of the syringe cylinder 22 near the upper end of the cylinder, and thereby provides an operator handle for mounting and removing the syringe cartridge 21 from the pump housing in the manner to be hereinafter described in further detail.

At the end of the piston rod 24 remote from the piston head 54, the longitudinal flanges 24a, 24b are partially cut-away to define surfaces 24d and in order to provide clearance for insertion into the coupling shoe 26. In addition, this same end of the piston rod 24 is provided with a pair of integral, outwardly and oppositely extending, cylindrical mounting bosses 59, one boss projecting perpendicularly outward from the outside face of the flange 24a, the other boss likewise projecting outward from the flange 24b.

A second pair of outwardly extending mounting bosses 61, parallel to the first set of mounting bosses 59 on the piston rod 24, are integral with the syringe cylinder 22 near the upper end of the cylinder.

As best observed in FIGS. 3, 5 and 6, the piston rod mounting bosses 59 are adapted to engage and be retained by the mounting and coupling shoe 26 which is secured to the leading end of the linear drive shaft 27 adapted to be coupled to the piston rod 24 for driving the syringe cartridge 21 through successive fill and pump strokes. The coupling shoe 26 includes a pair of confronting, wide mouth guide slots 63 in upstanding flanges 62, disposed on opposite sides of the coupling shoe, and adapted to engage and guide the mounting bosses 59 so that the syringe cartridge 21 can be inserted into the coupling shoe horizontally.

Hence, during the cartridge installation procedure, the tab 58 of the syringe cartridge 21 is gripped by two fingers of one hand of the operator and, with the longitudinal axis of the syringe cartridge held horizontally, the piston rod 24 and mounting bosses 59 are inserted horizontally into the guide slots 63 of the coupling shoe 26 (with the cutaway surfaces 24d of the piston rod directed downward) and moved to the rear of the coupling shoe which essentially defines a mounting yoke for the bosses 59. The syringe cartridge 21 is then rotated upwardly, about an axis of rotation through the mounting bosses 59 in the coupling shoe 26, so that the longitudinal axis of the syringe cartridge is brought into a vertical position, as illustrated by the solid lines in FIG. 3. The latter procedure brings the cut-away, lower end of the piston rod 24 into a retention channel 64 within the coupling shoe 26. In this regard, the cut-away surfaces 24d of the piston rod are rotated into abutment with a ledge 64a of the retention channel 64.

When the syringe cartridge 21 has been thus installed, the mounting bosses 59 in the guide slots 63 prevent the syringe cartridge from being dislodged vertically, whereas the cut-away surfaces 24d in the retention channel of the coupling shoe 26 prevent the cartridge from being dislodged horizontally.

As best observed in FIGS. 1 and 3, the mounting bosses 61 of the syringe cylinder 22 are adapted to engage a pair of fixed guide and retaining slots 66 provided in opposite walls of the syringe receiving compartment of the pump housing. By controlling the initial location of the coupling shoe 26, relative to the curved, wide mouth guide and retaining slots 66, the pumping apparatus can be conditioned to receive the syringe cartridge 21 only if its piston 23 is in a predetermined position within the syringe cylinder 22, i.e., in the top dead center position adapted to initially perform an intake stroke to fill the syringe with liquid. The latter is the proper state of the syringe for initial start-up of the pumping apparatus.

The intake and output I.V. tubes, 33, 34, respectively, from the syringe cartridge 21, are then passed vertically over the tube pincher blades 43a, 44a and are clamped in position by the closing of the tubing compartment access door 45 which is then latched shut by the latch 45b to firmly anchor and maintain the syringe cartridge in position during the operational cycles of the pump. The tubing access door 45 must be unlatched and opened to enable the syringe cartridge 21 to be rotated from the vertical position to a horizontal position for removal from the coupling shoe 26, whenever it is desired to replace the cartridge.

The coupling shoe 26 is, as previously indicated, secured to the upper end of the linear drive shaft 27 which advances and retracts the coupling shoe and thereby advances and retracts the piston rod 24 and piston 23 within the cylinder 22 for repetitive fill and pump strokes. As best observed in FIGS. 3 and 4, the linear drive shaft 27 is of non-circular cross-section and, in the preferred embodiment shown, is of rectangular cross-section. The drive shaft 27 passes through and is in sliding engagement with an anti-rotation bearing 68 having an opening of complimentary cross-section, and enabling the drive shaft to move along its longitudinal axis while being keyed against rotation about that axis.

A lead screw 70 is integral with, or otherwise appropriately secured to, the drive shaft 27 and is advanced and retracted along its longitudinal axis, to thereby advance and retract the drive shaft 27, by an internally threaded gear 72 in the gear train 31 driven by the motor 29. The gear 72 is appropriately supported for rotation in a pair of stationary gear carriers or thrust bearings 73, 74.

As best observed in FIGS. 1 and 3, a visual running indicator is provided in the form of a rotating disc 76 having a plurality of visually observable, preferably uniformly spaced, vertical index lines 77 located along its entire peripheral edge. The disc 76 is secured to a central bushing 78 (through which the lead screw 70 passes freely) and is journaled for rotation in the upper gear carrier 73. The bushing 78 and disc 76 are driven by the output shaft 29a of the motor 29 via a belt drive in the form of a simple O-ring 79 which passes around the output shaft of the motor and around the bushing 78 to provide a simple friction drive.

The peripheral index lines 77 are readily observable through a window 81 in the pump housing. Hence, when the pumping apparatus is operating at a very low pumping rate, so that no movement of the coupling shoe 26 or piston rod 24 is visually discernible by the operator, the rotation of the running indicator disc 76 will be apparent through the window 81 to assure the operator that the system is in operation.

Referring now more specifically to FIGS. 1 and 2, a motor rotation sensor 83 is provided to insure proper detection of a stalled motor 29 so that, in cooperation with the electrical control system, an alarm condition can be appropriately generated. Such motor stalling has a greater probability of occurring when the pump is used with a downstream filter which may clog and induce high back pressure on the pumping system.

The rotation sensor 83 comprises a disc 84 mounted on the output shaft 29a of the motor 29 for rotation therewith, the disc having alternate transparent and opaque sectors 85, 86, respectively. A photocell 87 detects light passing through the disc 84 from a reference light source 88, as the disc rotates, and generates electrical pulses which are appropriately directed to the electrical control system for monitoring and alarm functions. Hence, the rotation sensor 83 is capable of indicating any stalled motor condition.

As best observed in FIGS. 10 and 11, the pumping system, including the syringe cartridge 21, may embody appropriate means for indicating proper installation of the syringe cartridge and for detecting the presence of gas bubbles. In this regard, the inlet nipple 51 of the syringe cartridge 21 is surrounded by an integrally molded, transparent flag member 89. A fixed light source 91 and photoelectric sensor 92, both located in fixed positions within the syringe compartment of the pump housing, provide a reference light beam which is selectively interrupted by the flag member 89 whenever the syringe cartridge 21 has been properly positioned in the syringe compartment of the pump housing. In this regard, the flag 89 prevents the reference light beam from reaching the sensor 92 by interposing a totally reflecting surface 89a in the path of the light beam to deflect the light beam away from the sensor.

In addition, bubble detection is accomplished in the arrangement of FIG. 11 by providing a fixed light source 94 and photoelectric sensor 95 on opposite sides of the inlet nipple 51, so that gas bubbles passing through the nipple will interrupt the light beam and generate an appropriate electrical signal. The latter signal is appropriately transmitted to the electrical control system to bring about the generation of an alarm state. Hence, the bubble detection system insures no air bubbles are entering the syringe through the inlet nipple 51.

An alternative embodiment of a suitable system for monitoring the proper insertion of the syringe cartridge 21 within the syringe compartment is shown in FIG. 12. In this embodiment, a syringe nipple 151 is appropriately provided with an opaque, typically black, outer coating 151a so that, when the cartridge has been properly installed, a reference light beam from a fixed light source 191 in the pump housing is interrupted. This causes an appropriate electrical signal to be generated by a fixed photosensor 192 located in the pump housing on the opposite side of the nipple 151.

The new and improved syringe pump drive system and disposable syringe cartridge of the present invention satisfies a long existing need in the medical arts for improved, relatively simple, economical, reliable, stable and accurate syringe pumping systems.

It will be apparent from the foregoing that, while particular forms of the invention have been illustrated and described, various modifications can be made without departing from the spirit and scope of the invention. Accordingly, it is not intended that the invention be limited, except as by the appended claims.

I claim:

1. For use in a syringe pump having a housing and a syringe mounting, a syringe, comprising:
    a hollow cylinder having an open end and a closed end, said cylinder being adapted for normal use with its longitudinal axis substantially vertical, said cylinder having a pair of integral, parallel inlet and outlet nipples projecting from said closed end of said cylinder, said nipples being disposed on opposite sides of said cylinder with the axes of said nipples being substantially parallel to said longitudinal axis of said cylinder, there being no valves within said nipples, the uppermost interior surface of said cylinder being sloped upwardly in a single plane, said outlet nipple being located adjacent the highest point within said cylinder;
    a piston head with said cylinder; and
    a piston rod connected to said piston head and integral therewith for reciprocating said piston head along said longitudinal axis of said cylinder.

2. Apparatus as set forth in claim 1, wherein said piston rod has a pair of integral, outwardly extending mounting bosses adapted to engage the mounting means of a piston drive system.

3. Apparatus as set forth in claim 1, wherein said cylinder has a pair of integral, outwardly extending mounting bosses adapted to engage mounting means in a syringe receiving compartment.

4. Apparatus as set forth in claim 1, and further including a flexible sealing cap overlying and encasing said piston head, said cap defining a piston face, said sealing cap having a limp membrane skirt adapted to seal said open end of said cylinder without stretching at any time during reciprocation of said piston head.

5. For use in a syringe pump having a housing and a syringe mounting, a syringe, comprising:
    a hollow cylinder having an open end and a closed end, said cylinder being adapted for normal use with its longitudinal axis substantially vertical, said cylinder having a pair of inlet and outlet nipples projecting from said closed end of said cylinder, said nipples being disposed on opposite sides of said cylinder with the axes of said nipples being substantially parallel to said longitudinal axis of said cylinder, the uppermost interior surface of said cylinder being sloped upwardly in a single plane, said outlet nipple being located adjacent the highest point within said cylinder;
    a piston head within said cylinder;
    a piston rod connected to said piston head for reciprocating said piston head along said longitudinal axis of said cylinder; and
    a flexible sealing cap overlying and encasing said piston head, said cap defining an upwardly directed conical piston face, the slope of said conical face conforming to the slope of said interior surface of said cylinder.

6. For use in a syringe pump, a syringe, comprising:
    a hollow cylinder;
    a piston head within said cylinder;
    a piston rod connected to said piston head for reciprocating said piston head along the longitudinal axis of said cylinder; said piston rod having a pair of integral, outwardly extending mounting bosses at the opposite end of said piston rod from said piston head, said piston rod further having at the same end as said bosses a cut-away portion adjacent the bosses and extending along one side thereof, said mounting bosses and said cut-away portion constituting means for engaging the mounting means of a piston drive system in only a single position, said syringe being rotatable about an axis of rotation through said mounting bosses to lock said syringe in its operative position with its longitudinal axis positioned vertically and retained by said mounting means for operation of said syringe through repetitive fill and pump cycles.

7. Apparatus as set forth in claim 6, wherein said cylinder, said piston head, and said piston rod are molded plastic.

8. Apparatus as set forth in claim 6, wherein said piston rod has a substantially H cross-section perpendicular to the longitudinal axis of said piston rod.

9. Apparatus as set forth in claim 6, wherein said piston rod includes a pair of parallel longitudinally extending flanges joined by an integral crossbar.

10. Apparatus as set forth in claim 8 and further including a flexible sealing cap overlying and encasing said piston head, said cap defining a piston face, said sealing cap having a limp membrane skirt adapted to seal said open end of said cylinder without stretching at any time during reciprocation of said piston head.

11. For use in a syringe pump having a housing and a syringe mounting, the combination comprising:
    a syringe having a piston and piston rod, said piston rod having a pair of integral, outwardly extending mounting bosses adjacent a cut-away portion of said piston rod; and
    a coupling shoe defining a yoke with a passageway for receipt of said mounting bosses, said yoke and said mouting bosses together defining locking means enabling rotation of said syringe in only one direction to an operable position and restraining said syringe against dislocation relative to said coupling shoe while said syringe is in said operable position.

12. For use in a syringe pump, a disposable syringe cartridge, comprising:

a hollow cylinder having an open end and a closed end, said cylinder being adapted for normal use with its longitudinal axis substantially vertical, said cylinder having a pair of integral, parallel inlet and outlet nipples projecting from said closed end of said cylinder, said nipples being disposed on opposite sides of said cylinder with the axes of said nipples being substantially parallel to said longitudinal axis of said cylinder, there being no valves within said nipples, the uppermost interior surface of said cylinder being sloped upwardly in a single plane, said outlet nipple being located adjacent the highest point within said cylinder;

a piston head within said cylinder, said piston head having spaced apart parallel annular flanges;

a piston rod connected to said piston head and integral therewith for reciprocating said piston head along said longitudinal axis of said cylinder, said piston rod having a pair of integral, outwardly extending mounting bosses adjacent a partially cut-away portion of said piston rod, said mounting bosses and said cut-away portion being adapted to engage the mounting means of a piston drive system, whereby said syringe can be mounted within the longitudinal axis of said syringe horizontal, said syringe being then rotatable about said mounting bosses so that said longitudinal axis of said syringe is positioned vertically and retained by said mounting means for operation of said syringe through repetitive fill and pump cycles; and a flexible sealing cap overlying and encasing said piston head, said cap engaging said annular flanges and defining an upwardly directed conical piston face, the slope of said conical face conforming to the slope of said interior surface of said cylinder, said sealing cap further defining a pair of axially spaced apart sealing rings in engagement with the interior surface of said cylinder, said sealing cap having a limp membrane conical skirt adapted to seal said open end of said cylinder without stretching at any time during reciprocation of said piston head, said piston rod and said sealing cap, said skirt terminating in a thickened bead portion adapted to grip the external surface of said cylinder and prevent said sealing cap from being dislodged.

13. Apparatus as set forth in claim 12, wherein said cylinder, said piston head, and said piston rod are molded plastic.

14. Apparatus as set forth in claim 12, wherein said sealing cap is rubber.

15. Apparatus as set forth in claim 12, wherein said cylinder includes an integral tab for use as a handle in installing and removing said syringe cartridge from the syringe pump.

16. Apparatus as set forth in claim 12, wherein said syringe cartridge further includes a pair of I.V. tubes, one of said tubes being connected to said inlet nipple, the other of said tubes being connected to said outlet nipple.

17. Apparatus as set forth in claim 12, wherein said piston rod has a substantially H cross-section perpendicular to the longitudinal axis of said piston rod.

18. Apparatus as set forth in claim 12, wherein said piston rod includes a pair of parallel longitudinally extending flanges joined by an integral crossbar.

19. Apparatus as set forth in claim 12, wherein said annular flanges of said piston head are supported by a plurality of intersecting ribs.

20. Apparatus as set forth in claim 19, wherein said intersecting ribs intersect at the longitudinal axis of said piston head, the uppermost ends of said intersecting ribs being tapered to provide support for said conical face of said sealing cap.

* * * * *

UNITED STATES PATENT OFFICE
CERTIFICATE OF CORRECTION

Page 1 of 2

Patent No. 3,993,061     Dated November 23, 1976

Inventor(s) Stephen H. O'Leary

It is certified that error appears in the above-identified patent and that said Letters Patent are hereby corrected as shown below:

Column 1, line 57, delete "aforesaid" and insert therefor --aforedescribed--.

Column 2, line 12, delete "periatric" and insert therefor --pediatric--.

Column 6, line 13, delete "lin" and insert therefor --line--.

Column 7, lines 44-46, delete the sentence beginning "A copy of" and ending "Appendix A."; line 62, delete "adefine" and insert therefor --define--.

Column 8, lines 9-11, delete the sentence beginning "A copy" and ending "Appendix B.".

Column 13, line 53, delete "with" and insert therefor --within--.

Column 14, line 55, delete "8" and insert therefor --6--.

UNITED STATES PATENT OFFICE
CERTIFICATE OF CORRECTION
Page 2 of 2

Patent No. 3,993,061                    Dated November 23, 1976

Inventor(s) Stephen H. O'Leary

It is certified that error appears in the above-identified patent and that said Letters Patent are hereby corrected as shown below:

Column 15, line 1, delete "mouting" and insert therefor --mounting--; line 33, delete "within" and insert therefor --with--.

Signed and Sealed this

Twenty-second Day of November 1977

[SEAL]

Attest:

RUTH C. MASON  
Attesting Officer

LUTRELLE F. PARKER  
Acting Commissioner of Patents and Trademarks